United States Patent [19]
Keatley

[11] 4,442,837
[45] Apr. 17, 1984

[54] TWEEZERS FOR THE REMOVAL OF PARASITES FROM ANIMALS

[76] Inventor: Lawrence A. Keatley, 553 N. Harrison St., Fort Bragg, Calif. 95437

[21] Appl. No.: 353,372

[22] Filed: Mar. 1, 1982

[51] Int. Cl.³ .............................................. A01M 3/00
[52] U.S. Cl. .................................... 128/354; 128/321; 128/303 R; 128/1 R; 81/43; 43/134
[58] Field of Search ........................ 128/354, 321-324, 128/355, 303 R, 1 R; 33/27 B; 119/87; 81/43; 43/133-134, 142

[56] References Cited

U.S. PATENT DOCUMENTS

| | | | |
|---|---|---|---|
| 1,108,299 | 8/1914 | Wisman | 81/43 |
| 2,212,013 | 8/1940 | Devareaux | 81/43 |
| 2,663,936 | 12/1953 | Lepkowski | 33/27 B |
| 2,876,778 | 3/1959 | Kees | 128/321 |
| 4,163,340 | 8/1979 | van der Merwe | 43/134 |
| 4,213,460 | 7/1980 | Weiner | 128/355 |

Primary Examiner—C. Fred Rosenbaum
Assistant Examiner—Gene B. Kartchner
Attorney, Agent, or Firm—Melvin R. Stidham

[57] ABSTRACT

A pair of tweezers that can be closed over and locked in place on a parasite by moving a slide lock with one hand. With the tweezers locked closed, one can slide the same hand up to grasp a knob and turn the tweezers to remove the parasite.

3 Claims, 2 Drawing Figures

TWEEZERS FOR THE REMOVAL OF PARASITES FROM ANIMALS

BACKGROUND OF THE INVENTION

The most effective way to remove many parasites, such as the tick, from animals is to grasp the parasite and pull it free. It has also been found that by rotating the tick smoothly, it is more easily dislodged from the host animal. For this purpose, there is a need for an instrument which can effectively be operated with one hand while the other hand of the operator is used to restrain the host animal and to part the fur and manipulate the skin surrounding the parasite. The instrument should also be effective to turn the parasite, causing it to release its grip on the host animal with a minimal amount of damage to the parasite and, hence, to the host animal.

OBJECT OF THE INVENTION

It is an object of this invention to provide a pair of tweezers that is effective for removal of parasites from animals wherein only one hand is required to operate the tweezers while the other hand is free to restrain the animal, part the fur and manipulate the skin.

It is a further object of this invention to provide a pair of tweezers that can be closed, and locked in closed position by manipulation of one hand of the operator.

The further object of this invention to provide tweezers for the removal of animal parasites that can be closed, and turned while gripping the parasite by use of just one hand.

Other objects and advantages of this invention become apparent from the description to follow, particularly when read in conjunction with the accompanying drawing.

SUMMARY OF THE INVENTION

In carrying out this invention, I provide tweezers which comprise a pair of legs of flexible steel or the like which are joined at their upper ends, on which is carried a thumb ring. Camming surfaces are provided on the outside of the legs, and a lock sleeve, which is slidable along these surfaces by pulling or pushing it with the fore and index fingers, presses the legs together or allows them to flex apart. In the lower position of the lock sleeve, the legs are fully opened, while in the upper position, they are held closed. In this position, the hand is simply moved along the body of the tweezers until it engages a knob at the top of the thumb ring, whereby the knob may be turned between the thumb and forefinger to rotate the tweezers and parasite, forcing the parasite to release.

DESCRIPTION OF A PREFERRED EMBODIMENT

Figure 1:
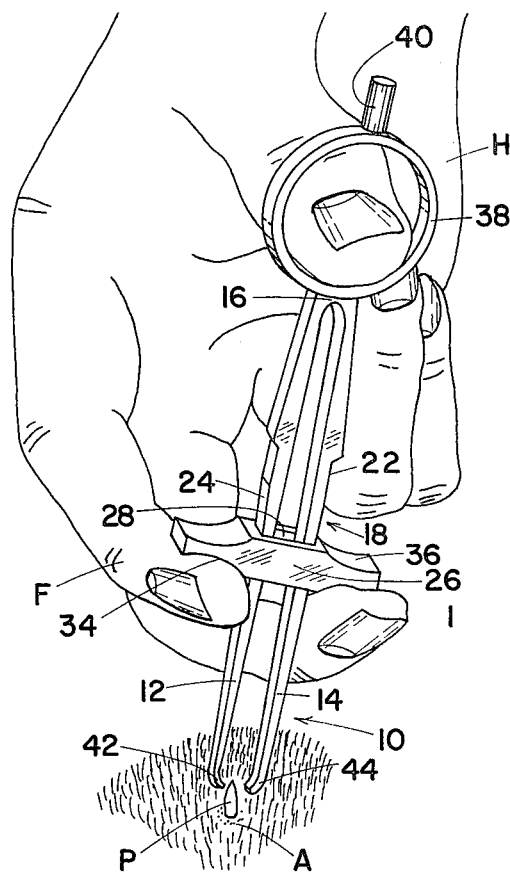
FIG. 1 is a view in perspective of the tweezers in full open position.
Figure 2:
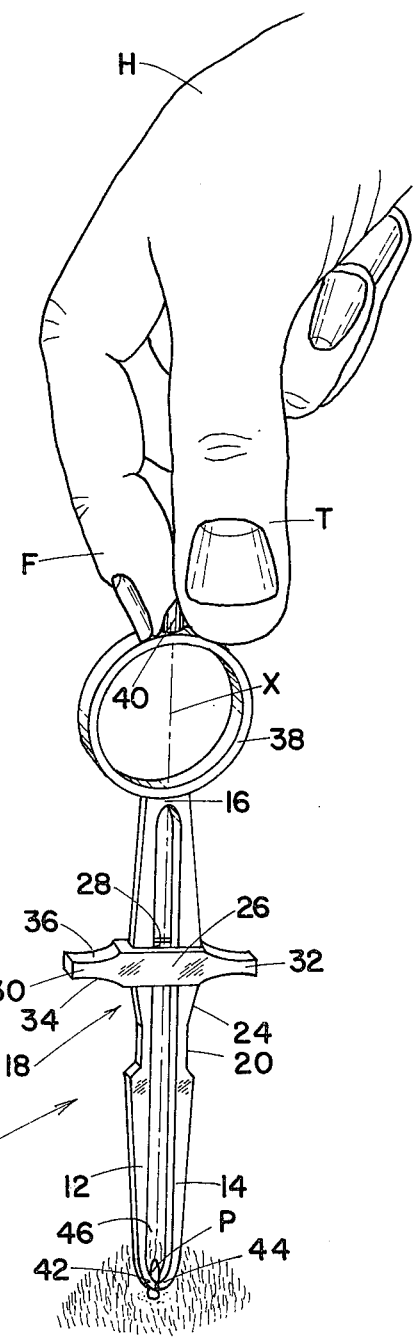
FIG. 2 is a view in perspective showing the tweezers locked in closed position gripping on an animal parasite.

Referring now to the drawing with greater particularity, the pair of locking tweezers 10 of this invention comprises a pair of legs 12 and 14 of a flexible material, such as a spring steel, enabling them to be flexed together to the position shown in FIG. 2 and then released to spread apart to their normal, open position shown in FIG. 1. The legs 12 and 14 are joined at their upper ends 16, as by forming them integrally from a single piece of metal.

Formed on the outsides of the legs 12 and 14 are camming surfaces 18, including a pair of inset, lower, generally parallel, flat lock-open surfaces 20, a pair of upper flat, generally parallel, lock-closed surfaces 22 (FIG. 1), and intermediate diverging actuating traversing surfaces 24. Engaged over the camming surfaces 18 is a lock sleeve 26 with a rectangular opening 28 that receives the legs 12 and 14.

Lateral extensions 30 and 32 on the lock slide 26 are provided with lower and upper gripping surfaces 34 and 36, which surfaces may be engaged by the fore and index fingers, F and I of one hand H of the operator, respectfully, to raise and lower the lock sleeve 26. With the lock sleeve in its lower position, shown in FIG. 1, the inset flat portions 20 are allowed to engage the ends of the opening 28 to enable the legs to spread to their open position. With the lock slide 26 pulled to its upper position shown in FIG. 2, the more widely separated upper flat portions 22 are engaged, retaining the legs in their closed positions.

Operation of the lock slide 26 is facilitated by provision of a thumb ring 38 which is welded or otherwise secured to the top 16 of the legs 12 and 14 so that a diameter of the ring lies on the vetical axis X, about which the legs 12 and 14 are symetrical. Also lying on the axis X is a knurled thumb knob 40 which, as shown in FIG. 2, may be grasped between the thumb T and forefinger F to turn the tweezers 10 about the axis X.

The lower ends 42 and 44 of the legs 12 and 14 are bent inwardly, as shown to provide converging gripping surfaces which can engage around the neck segment of the parasite P, the head of which may be embedded in the host animal A. The diverging nature of the ends 42 and 44 provide a space 46 between the legs 12 and 14 when in closed position to accomodate the expanding body of the feeding parasite, such as a tick.

In operation, the tweezers 10 are gripped as shown in FIG. 1 with the thumb T in the thumb ring 38 and the forefinger F and index finger I engaged under the lock slide 26 while the gripping points 42 and 44 are positioned over the feeding parasite P. It should be noted that the tweezers 10 can be gripped in this manner with just one hand of the operator while the other hand (not shown) may be used to restrain the animal, part its fur and manipulate its skin to facilitate operation of the tweezers.

Then, with the tweezers positioned over the parasite P, the lock slide 26 is pulled upwards to the position shown in FIG. 2 wherein the inner surfaces 28 of the lock slide move up the diverging cam surfaces 24 to force the legs 12 and 14 together over the parasite P. When the lock slide 26 reaches the upper flat portions, the legs 12 and 14 are locked in their closed positions. In this position, the same hand of the operator O is simply moved upward to grasp the knob 40, which is then rotated between the thumb T and forefinger F about the axis X to turn the parasite P, causing it to lose its hold without damage to itself or to the host animal A.

While this invention has been described in conjunction with a preferred embodiment thereof, is obvious tat modifications and changes therein may be made by those skilled in the art to which it pertains, without departing the scope of this invention, as defined by the claims appended hereto.

What is claimed as invention is:

1. Tweezers for the removal of parasites from animals comprising:
   a pair of flexible legs fixedly joined at their upper ends;
   inwardly directed gripping portions on the distal ends of said legs; and
   said gripping portions being normally separated but being engageable by squeezing said legs to flex them toward each other;
   camming surfaces on the outside of said legs intermediate the ends thereof;
   said camming surfaces including:
   generally parallel open-leg, flat surfaces formed inward from the lateral surfaces of said legs toward the distal ends thereof;
   generally parallel, closed-leg, flat lock surfaces near the lateral surfaces of said legs toward the joint between them; and
   intermediate actuating surfaces diverging upward from said open-leg surface to said close-leg lock surfaces;
   said tweezers further including:
   a lock slide embracing said legs to slidably engage over said camming surfaces so that when raised from said open-leg surfaces it flexes said legs together and holds said gripping portions together when at said closed-leg lock surfaces;
   a thumb ring secured to the joint between said legs;
   a lateral extension on said lock slide the underside of which is engagable by a person's finger on one hand while the thumb of the same hand is positioned in said thumb ring thereby to raise said lock slide; and
   a knob fixed to the top of said thumb ring to be engaged by the thumb and a finger of said same hand while said lock slide is at said closed-leg lock surfaces to turn said legs about a longitudinal axis extending between them.

2. The tweezers defined by claim 1 wherein there are:
   a pair of lateral extensions on said lock slide to be engaged by the fore and index fingers of said hand.

3. Tweezers defined by claim 1 wherein:
   the gripping portions of said legs are curved toward each other so that there is a space between said legs above said distal ends to accommodate the body of an animal parasite.

* * * * *